(12) United States Patent
Hirashima (10) Patent No.: US 12,109,092 B2
(45) Date of Patent: Oct. 8, 2024

(54) RESTORING FORCE PRESERVING PORTION-BONDED MEDICAL TAPE AND METHOD FOR MANUFACTURING THE SAME

(71) Applicant: YUGENKAISHA CHOURYU, Kosai (JP)

(72) Inventor: Toshifumi Hirashima, Shizuoka (JP)

(*) Notice: Subject to any disclaimer, the term of this patent is extended or adjusted under 35 U.S.C. 154(b) by 0 days.

(21) Appl. No.: 17/759,190

(22) PCT Filed: Mar. 17, 2022

(86) PCT No.: PCT/JP2022/012144
§ 371 (c)(1),
(2) Date: Nov. 20, 2023

(87) PCT Pub. No.: WO2022/220008
PCT Pub. Date: Oct. 20, 2022

(65) Prior Publication Data
US 2024/0082068 A1 Mar. 14, 2024

(30) Foreign Application Priority Data
Apr. 13, 2021 (JP) .................... 2021-067909

(51) Int. Cl.
*A61F 13/02* (2024.01)
(52) U.S. Cl.
CPC ...... *A61F 13/0283* (2013.01); *A61F 13/0269* (2013.01)
(58) Field of Classification Search
CPC .................................................. A61F 13/0283
See application file for complete search history.

(56) References Cited

U.S. PATENT DOCUMENTS

2021/0245452 A1* 8/2021 Boroughs ............ B65H 23/044

FOREIGN PATENT DOCUMENTS

| JP | 2018-007748 A | 1/2018 |
|----|---------------|--------|
| JP | 6312915 B1 | 4/2018 |
| JP | 6832470 B | 2/2021 |

OTHER PUBLICATIONS

ISR: Japanese Patent Office; May 23, 2022.

* cited by examiner

*Primary Examiner* — Dah-Wei D. Yuan
*Assistant Examiner* — Andrew J Bowman
(74) *Attorney, Agent, or Firm* — Patshegen IP; Moshe Pinchas

(57) ABSTRACT

Provided is a medical tape that has a high effect of alleviating a persistent skin irritation during an application duration caused by a residual shrink force associated with a forming shrinkage.
A medical tape includes an elastic base member portion film-formed of a solution polymer and having an elastic function, a restoring force preserving portion having inelastic, flexible, and restorable functions, an adhesion portion having a function to apply and hold the elastic base member portion on a skin, and a release portion having a function to protect the adhesion portion. The restoring force preserving portion, the elastic base member portion, the adhesion portion, and the release portion are laminated in this order from an upper layer.

1 Claim, 3 Drawing Sheets

RESTORING FORCE PRESERVING PORTION-BONDED MEDICAL TAPE AND METHOD FOR MANUFACTURING THE SAME

TECHNICAL FIELD

The present invention relates to a restoring force preserving portion-bonded medical tape and method for manufacturing the same.

BACKGROUND ART

Conventionally, for medical industries or the like, a medical tape that uses a film material, such as a polyurethane film, having a function excellent in waterproof performance, moisture permeability, skin followability, and the like has been selected in order to cover and fix a gauze and a pad, fix a surgical tool, such as an indwelling needle or a catheter, cover and protect a wound or a skin, and the like. The indwelling needle is an injection needle used by being inserted into a vein and fixed to a body for blood sampling or drip infusion. The indwelling needle is also used in drip infusion or the like used for about a week.

Since these film materials have a very thin thickness of approximately 10 μm, it cannot independently hold a planar shape and is easily rounded under a natural environment. For this reason, as a support for holding the planar shape, a shape protection cover having stiffness higher than that of an elastic base member of the film material, such as an inelastic plastic film, is laminated with the film material in order to hold the planar shape and prevent formation of wrinkles or the like.

Note that, in its manufacturing process, as means to laminate the support for holding the planar shape and the film material, there has been widely used a method in which, after applying a mixed liquid (a urethane resin liquid and a crosslinking agent liquid) that serves as a raw material of the polyurethane film on an upper layer (one surface) of the inelastic plastic film, the mixed liquid is hardened to form a film, and thus, the polyurethane film is obtained, and simultaneously, the support for holding the planar shape and the film material are laminated.

However, since the above-described method simultaneously performs the film formation of the polyurethane film and the lamination on the support, there is generated a shrink force (an internal stress) remaining due to a forming shrinkage associated with the hardening of the mixed liquid serving as the raw material of the polyurethane film in the polyurethane film. Hereinafter, the "shrink force remaining in the elastic base member during the manufacturing process" will be referred to as a "residual shrink force." Accordingly, in the medical tape that uses the polyurethane film obtained in the above-described method as the elastic base member of the medical tape and the inelastic plastic film as the support of the medical tape, that is, "the medical tape formed by simultaneously performing the film formation of the elastic base member in a film form and the lamination on the inelastic support positioned on an upper layer using the mixed liquid (the urethane resin liquid and the crosslinking agent liquid) serving as the raw material of the polyurethane film, applying an adhesion on a lower layer of the elastic base member, providing an inelastic release sheet on the lowermost layer, and providing an inelastic support for holding the planar shape on an upper layer of the elastic base member" (hereinafter, referred to as a "support-bonded medical tape using inelastic material as the support"), the residual shrink force associated with the forming shrinkage resides in the film material as the elastic base member. That is, when the mixed liquid serving as the raw material of the elastic base member is not attached on the support of the inelastic material, the mixed liquid serving as the raw material of the elastic base member freely shrinks, and thus, the residual shrink force is not generated. Meanwhile, when the mixed liquid serving as the raw material of the elastic base member is well attached on the support of the inelastic material, the mixed liquid serving as the raw material of the elastic base member cannot freely shrink except in a film thickness direction, and thus, the residual shrink force is generated near an attachment interface between the elastic base member and the support of the inelastic material after the film formation.

Note that the support-bonded medical tape using inelastic material as the support is applied in the following sequence: 1) remove the release sheet; 2) apply the tape on a skin; and 3) remove the support. In addition, the residual shrink force of the support-bonded medical tape using inelastic material as the support is not eliminated even by entirely removing the release sheet. After the tape is applied on the skin, the residual shrink force is released by removing the support, and acts as a force to continuously shrink the skin. Since the skin is shrunken, the residual shrink force causes a persistent skin irritation during the application duration.

Figure 1:
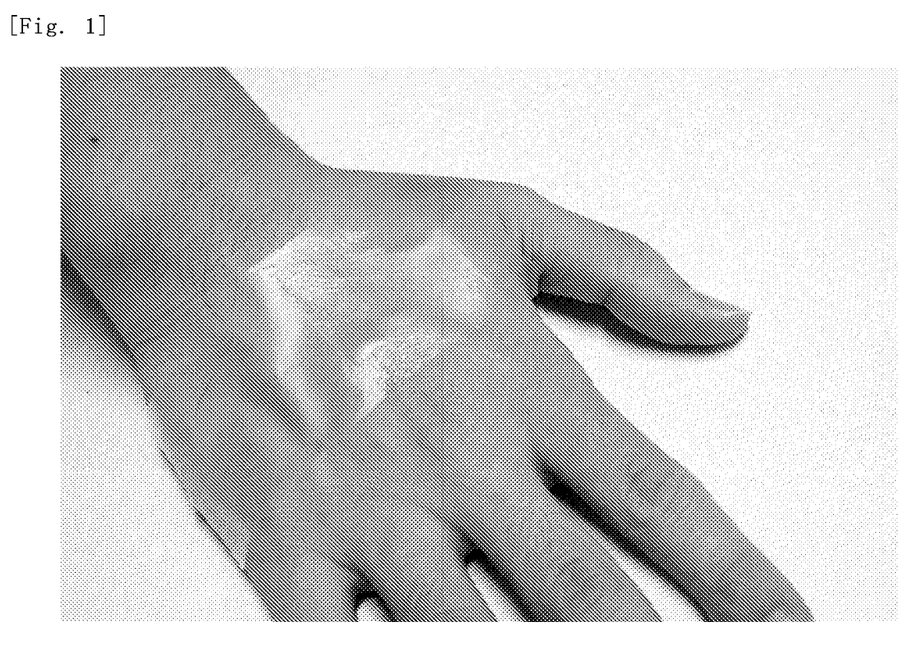
FIG. 1 is an explanatory diagram illustrating a state in which an inelastic support of a thumb side used for checking the residual shrink force is removed.
Figure 2:
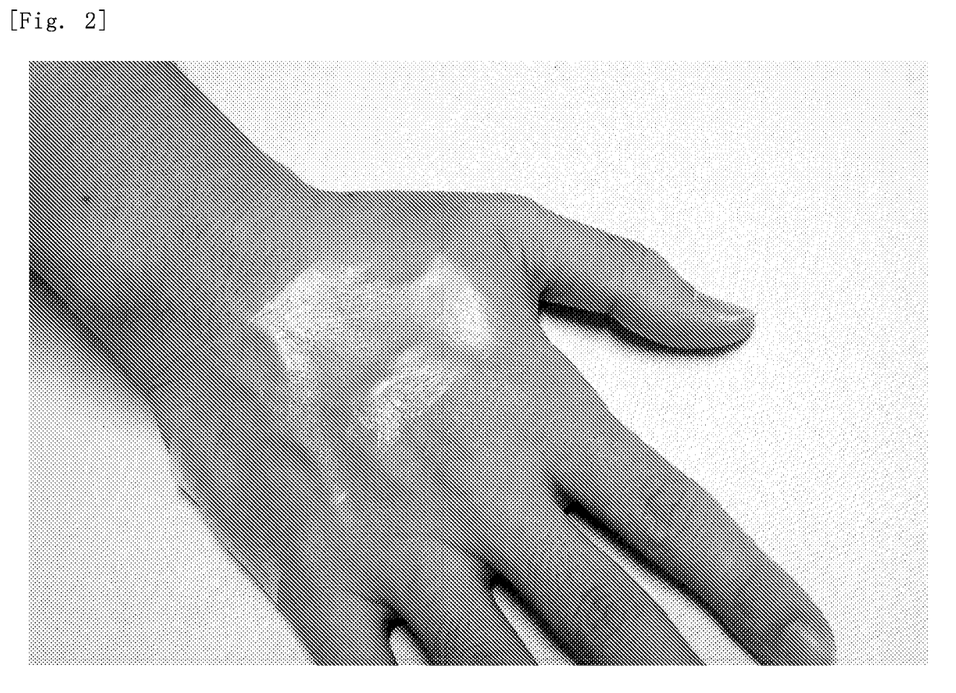
FIG. 2 is an explanatory diagram illustrating a state in which a support of a fifth finger side as a remaining inelastic support in the explanatory diagram illustrated in FIG. 1 is removed.

Here, the residual shrink force existing in the support-bonded medical tape using inelastic material as the support will be described with reference to FIGS. 1 and 2. FIG. 1 is an explanatory diagram illustrating a state in which after a support-bonded medical tape using inelastic material as the support having a bisected support structure is applied on a skin, a support of the thumb side is removed. In order to compare states of the elastic base members underlying the support of the thumb side and the support of the fifth finger side, the support of the thumb side is removed, and the support of the fifth finger side is not removed. While fine wrinkles are observed in the elastic base member of the thumb side from which the support is removed after the tape is applied on the skin, no change is observed in the elastic base member of the fifth finger side from which the support is not removed. FIG. 2 illustrates a state in which the remaining support, that is, the support of the fifth finger side is removed. In FIG. 2, fine wrinkles are also observed in the elastic base member of the fifth finger side. It is conceived that this is because, as the support is removed from the support-bonded medical tape using inelastic material as the support, the elastic base member is released from the support and shrunken so as to exhibit fine wrinkles in the elastic base member, and therefore, a residual shrink force associated with the forming shrinkage exists in the elastic base member. In this manner, in the support-bonded medical tape using inelastic material as the support, the residual shrink force is released by removing the support. Therefore, the residual shrink force associated with the forming shrinkage existing in the support-bonded medical tape using inelastic material as the support can be observed by after applying the medical tape on the skin, removing the support to shrink the elastic base member, thereby causing fine wrinkles to appear in the elastic base member.

Note that, in the medical tape industry, a warning, such as "please apply without pulling (without stretching) because it may cause skin irritation," is called in a handling manual or the like of the product. Therefore, in the medical tape industry, it is inferred that a risk of applying an elastic base member portion of an elastic medical tape on a skin in a "pulled and stretched state" should be sufficiently understood as a common sense of those skilled in the art. Additionally, in the plastic industry, it is conceived to be a common sense of those skilled in the art that applying a solution polymer on an upper layer of an inelastic support (for example, a plastic film), drying the solution polymer and forming a polyurethane film and laminating it on the support at the same time generates the residual shrink force (the internal stress) associated with the forming shrinkage within the polyurethane film.

On the other hand, in the medical tape industry, it is inferred that there is little recognition (a common sense of those skilled in the art) that the residual shrink force associated with the forming shrinkage exits within the polyurethane film as the elastic base member portion of the support-bonded medical tape using inelastic material as the support. If there is the recognition (the common sense of those skilled in the art) of the existence of the residual shrink force associated with the forming shrinkage in the medical tape industry, and it is understood that the residual shrink force has a harmful effect, there should be a description of warning or the like on the "residual shrink force associated with the forming shrinkage existing in the elastic base member portion" in a handling manual or the like of the product. In a handling manual or the like of a medical tape currently manufactured and sold, there is only a warning that says "if a symptom that seems to be a skin disorder (rash, redness, itching, and the like) appears during use of this product, please stop using and carry out an appropriate treatment," which is a warning that contains a problem of possibly misleading that it is caused by the user's constitutive endogenous cause. Accordingly, there has been a problem that, even though it is a medical tape used by a user with a purpose, the user himself uses the medical tape without recognizing the harmful effect associated with the "residual shrink force associated with the forming shrinkage existing in the elastic base member portion," and moreover, without any preventive measures. Furthermore, a root of this problem is that there is a contradiction that the "residual shrink force associated with the forming shrinkage" is the common sense of those skilled in the art in the plastic industry but it is not the common sense of those skilled in the art in the medical tape industry where products using similar materials are manufactured and sold, and there has been a problem that no countermeasure has been taken for the residual shrink force associated with the forming shrinkage having the harmful effect in the medical tape industry.

In a part, a medical tape (for example, see Patent Documents 1 and 2) for alleviating a persistent skin irritation during application duration of an elastic base member of an elastic medical tape has been proposed, and the persistent skin irritation during application duration of the support-bonded medical tape using inelastic material as the support caused by the residual shrink force is improved. However, in the medical tape described in Patent Document 1, in the manufacturing process, since it is essential to laminate the elastic base member portion and the stretch prevention portion in a state where the elastic base member portion is loosened or not extended, it is not possible to simultaneously form the film of the elastic base member portion and laminate the stretch prevention portion and the elastic base member portion, and problems such as manufacturing equipment and manufacturing cost have emerged in the manufacture of the medical tape, from the viewpoint of efficiency. Accordingly, in the conventional support-bonded medical tape using inelastic material as the support, the production that deals with the residual shrink force associated with the forming shrinkage is not easy, but generates the residual shrink force associated with the forming shrinkage in the elastic base member portion of the medical tape. Thus, it is not easy to alleviate the persistent skin irritation during application duration caused by the residual shrink force associated with the forming shrinkage, and the current situation is that there has been no means that can appropriately solve such a disadvantage.

CITATION LIST

Patent Document

Patent Document 1: Japanese Patent No. 6312915
Patent Document 2: Japanese Patent No. 6832470

SUMMARY OF INVENTION

In view of the aforementioned problems, it is therefore an object of the present invention to provide a medical tape that has a high effect of alleviating a persistent skin irritation during an application duration caused by a residual shrink force associated with a forming shrinkage of, in particular, a medical tape that has the forming shrinkage by using a solution polymer as a raw material and simultaneously performing a film formation and a lamination in a manufacturing process and aims to be applied on a skin that exhibits an excessive reaction even when a degree of residual shrink force associated with the forming shrinkage as a cause is an insignificant irritation so as to be described as of a level of magnifying lens or microscope, not as of a level of naked eye.

In order to solve the above problems, the present inventors have completed the present invention as a result of repeated diligent studies. That is, a restoring force preserving portion-bonded medical tape of the present invention includes an elastic base member portion film-formed of a solution polymer and having an elastic function, a restoring force preserving portion having inelastic, flexible, and restorable functions, an adhesion portion having a function to apply and hold the elastic base member portion on a skin, and a release portion having a function to protect the adhesion portion. The restoring force preserving portion, the elastic base member portion, the adhesion portion, and the release portion are laminated in this order from an upper layer. Additionally, according to the present invention, there is provided a method for manufacturing a medical tape, comprising: applying a solution polymer serving as an elastic base member portion having an elastic function to an upper layer of a restoring force preserving portion bent into an approximately arc shape or approximately bow shape having a projected cross-sectional shape by an external force and simultaneously performing a film formation of the elastic base member portion and a lamination of the restoring force preserving portion and the elastic base member portion to complete the film formation, obtaining the elastic base member portion, and obtaining an approximately arc-shaped or approximately bow-shaped two-layer structure having a projected cross-sectional shape, the two-layer structure being composed of the restoring force preserving portion and the elastic base member portion; and subsequently, removing the external force applied to the restoring force preserving portion to exert a restorability that the restoring force preserving portion has and obtaining a two-layer structure composed of the elastic base member portion and the restoring force preserving portion, the elastic base member portion being in a state where a residual shrink force generated in association with a forming shrinkage of the solution polymer is reduced by a restoring force associated with a shape change in a direction opposite to the residual shrink force generated in association with the forming shrinkage of the solution polymer. In the method for manufacturing the medical tape of the present invention, steps other than the above steps may be optional and are not particularly limited as long as the effects of the present invention can be obtained.

Advantageous Effects of Invention

The medical tape obtained by the method of production of the present invention ensures reducing the residual shrink force associated with the forming shrinkage in a manufacturing stage of the medical tape by introducing means for reducing the force to continuously shrink a skin caused by the residual shrink force associated with the forming shrinkage of, in particular, the medical tape that has the forming shrinkage by using the solution polymer as a raw material and simultaneously performing the film formation and the lamination in the manufacturing process to a medical tape as a function. Accordingly, when in use of the medical tape, the medical tape can be applied on a skin in a state where the residual shrink force associated with the forming shrinkage of the medical tape is reduced, and therefore, the force to continuously shrink the skin caused by the residual shrink force associated with the forming shrinkage of the medical tape can be reduced and the persistent skin irritation during the application duration caused by the residual shrink force can be alleviated. This ensures an application on the skin that exhibits an excessive reaction even when a degree of residual shrink force associated with the forming shrinkage as a cause is an insignificant irritation so as to be described as of a level of magnifying lens or microscope, not as of a level of naked eye, thereby ensuring providing a medical tape, an adhesive skin patch, and the like of low irritation. Furthermore, it is possible to prevent inflammation in sebaceous glands or sweat glands, inflammation in the root of hair or its surrounding tissues, a medical instrument pressure-related wound caused by poor blood circulation in the skin cells, capillary vessels, or the like due to pressure, and the like. With the medical tape manufacturing method of the present invention, the medical tape of the present invention can be efficiently manufactured.

BRIEF DESCRIPTION OF DRAWINGS

FIG. 5 is a drawing illustrating a manufacturing process of the medical tape according to the first embodiment of the present invention and is a schematic cross-sectional view illustrating a state of a step where a solution polymer serving as an elastic base member portion 2 having an elastic function is applied to an upper layer of the restoring force preserving portion 1 illustrated in FIG. 4, and a film formation of the elastic base member portion 2 and a lamination of the restoring force preserving portion 1 and the elastic base member portion 2 are simultaneously performed to complete the film formation, obtain the elastic base member portion 2, and obtain an approximately arc-shaped two-layer structure having a projected cross-sectional shape, which is composed of the restoring force preserving portion 1 and the elastic base member portion 2.

FIG. 6 is a drawing illustrating a manufacturing process of the medical tape according to the first embodiment of the present invention and is a schematic cross-sectional view illustrating a state of a step where the external force applied to the restoring force preserving portion 1 is removed by moving the two-layer structure obtained in FIG. 5 from the recess-shaped work table 5 to a work table 6 having a horizontal cross-sectional shape to exert a restorability that the restoring force preserving portion 1 has and obtain a two-layer structure composed of the elastic base member portion 2 in a state where a residual shrink force generated in association with a forming shrinkage of the solution polymer is reduced by a restoring force associated with a shape change in a direction opposite to the residual shrink force generated in association with the forming shrinkage of the solution polymer and the restoring force preserving portion 1.

DESCRIPTION OF EMBODIMENTS

In the course of diligent studies, the inventor found that a cause of a residual shrink force in a support-bonded medical tape using inelastic material as the support resided in a forming shrinkage caused by simultaneously performing a film formation and a lamination during manufacturing, and the residual shrink force of the support-bonded medical tape using inelastic material as the support was not eliminated even after a whole release sheet was removed, but after the medical tape was applied on a skin, the residual shrink force was released by removing the inelastic support to become a force that continuously shrinks the skin to shrink the skin, thereby causing a persistent skin irritation during application duration by the support-bonded medical tape using inelastic material as the support. Therefore, the inventor focused on, in the manufacturing process of the medical tape using a solution polymer as a raw material, means that reduces the residual shrink force associated with the forming shrinkage by dealing with the forming shrinkage caused by simultaneously performing the film formation and the lamination from a manufacturing stage.

Here, a skin irritation when the support-bonded medical tape using inelastic material as the support is used for the purpose to, for example, cover and protect wounds or skin will be described. The skin surface has openings of sebaceous glands or sweat glands and also hair. For this reason, the residual shrink force of the support-bonded medical tape using inelastic material as the support continuously deforms the openings of sebaceous glands or sweat glands and occasionally acts as an occluding force so as to generate inflammation (redness, swelling, fever, pain, and dysfunction) in sebaceous glands or sweat glands in some cases. In addition, the continuous skin shrinking force acts as a force to shrink a skin and persistently draw up the hair, so that inflammation occurs in the root of hair or its surrounding tissues in some cases.

Next, a skin irritation when the support-bonded medical tape using inelastic material as the support is used for the purpose to cover and fix a gauze, a pad and the like or fix a surgical tool, such as an indwelling needle or a catheter, will be described. The residual shrink force of the support-bonded medical tape using inelastic material as the support not only acts to fix the indwelling needle, the catheter, or the like but also acts as a force to persistently press a skin at the portion where the indwelling needle, the catheter, or the like is fixed. The residual shrink force is converted into a force of persistently pressing skin cells, capillary vessels, or the like via such surgical tools.

Next, the force of persistently pressing skin cells, capillary vessels, or the like will be described. For example, the blood vessels are stretched all over a human body, and its total extension length is approximately 100,000 km, which reaches around two and a half laps of the earth. In addition, nearly 95% of the blood vessels are capillary vessels. The capillary vessels have a diameter of approximately 7 μm and a wall thickness of 1 μm or smaller, which is significantly thin. For this reason, even for an unaware insignificant pressure, the capillary vessels of skin may be easily deformed or obstructed.

There are approximately five million red corpuscles, used to carry oxygen to cells over the entire body, per a microliter of blood. The red corpuscles are disk-shaped solid materials having recessed centers on both sides with a diameter of approximately 7 to 8 μm and a thickness of approximately 2 μm. The red corpuscles pass through the capillary vessels having a diameter of approximately 7 μm while they are deformed. However, since deformation of the red corpuscles as solid materials is limited, it is difficult to allow the red corpuscles to pass through the capillary vessels even when slight deformation occurs in capillary vessels. In addition, the capillary vessels may be clogged due to occlusion of red corpuscles in some cases. As a result, oxygen deficiency often occurs in cells due to poor blood circulation.

Poor blood circulation caused by pressure may generate a disease in which tissues or cells of skin locally die, such as a decubitus, so called a bedsore. Experimentally, it is said that a decubitus is generated if a persistent pressure is applied to a same part of a body for two hours or longer. For this reason, in order to prevent the decubitus from occurring in the medical industry, it is recommended that a posture be changed at approximately two hour intervals for a bedridden patient who is in a state of lying on a bed or the like, and at approximately thirty minute intervals for a patient who in a state of sitting on a wheelchair or the like. In this manner, the decubitus is generated due to poor blood circulation caused by pressure for several hours.

Furthermore, the recent support-bonded medical tapes using inelastic material as the support have been remarkably improved in skin followability, moisture permeability, waterproof property, skin adherence, and the like, compared with the conventional elastic medical tapes, so that they can be continuously bonded for about a week. For this reason, the support-bonded medical tape using inelastic material as the support are used in many cases to cover and fix a gauze, a pad, and the like, and in particular, fix an indwelling needle for drip infusion or the like for about a week. The force of persistently shrinking skin by covering the surgical tool acts as a force to persistently press a portion of the skin where a medical instrument, such as the indwelling needle or the catheter, is fixed for several days. Therefore, a medical instrument pressure-related wound and the like may occur in the fixed portion. This is inferred to be a period of time far exceeding a limitation of several hours for preventing the decubitus from occurring.

Due to improved qualities of adhesives and elastic base members, a long-time fixation with peel-off durability has been possible, and there has been a product that can be attached for a week or longer. In such a product less likely to be peeled off and excellent for long-time fixation, it is important to inform a warning "when removing the product, please gently remove the product along hair streaks so as not to harm skin" in the handling manual or the like. In order to alleviate skin irritation at the time of removing the product, means that does not forcibly peel the product but leaves it until it peels off is effective. However, use of the means that leaves the product until it peels off naturally increases the application duration, and the persistent skin irritation during the application duration caused by the residual shrink force continuously increases.

Note that, even for insignificant irritation, many patients complain of discomfort and distress. However, if insignificant irritation is persistently applied to the body, "hypaesthesia" which causes dull sensation to a stimulus occurs, so that the number of patients who complain of discomfort or distress is reduced. Although this is generally called "habituation," it does not mean that the stimulus to the body has disappeared, and deformation or occlusion generated in capillary vessels of skin, poor blood circulation, and the like are improved. Even though a degree of the residual shrink force associated with the forming shrinkage is an insignificant irritation that may be described as of a level of magnifying lens or microscope, not as of a level of naked eye, it can sufficiently be such a cause.

In this manner, in order to alleviate the persistent skin irritation during the application duration, it is important to take the process that leads to the forming shrinkage into consideration, bring into a state where the residual shrink force generated in association with the forming shrinkage at the time of the film formation is reduced in an elastic base member portion of a restoring force preserving portion-bonded medical tape, and reduce the force that continuously shrinks the skin due to the residual shrink force associated with the forming shrinkage. Here, in a manufacturing process of the restoring force preserving portion-bonded medical tape, a solution polymer serving as the elastic base member portion having an elastic function is applied to an upper layer of the restoring force preserving portion bent into an approximately arc shape having a projected cross-sectional shape by an external force using a work table having a recessed cross-sectional shape, and a film formation of the elastic base member portion and a lamination of the restoring force preserving portion and the elastic base member portion are simultaneously performed to complete the film formation, obtain the elastic base member portion, and obtain an approximately arc-shaped two-layer structure having a projected cross-sectional shape, which is composed of the restoring force preserving portion and the elastic base member portion. Next, the external force applied to the restoring force preserving portion is removed by moving the two-layer structure from the recess-shaped work table to a work table having a horizontal cross-sectional shape to exert a restorability that the restoring force preserving portion has and obtain a two-layer structure composed of the elastic base member portion in a state where a residual shrink force generated in association with a forming shrinkage of the solution polymer is reduced by a restoring force associated with a shape change in a direction opposite to the residual shrink force generated in association with the forming shrinkage of the solution polymer and the restoring force preserving portion. This process ensures obtaining the elastic base member portion in a state where the residual shrink force generated in association with the forming shrinkage of the solution polymer is reduced or eliminated. Then, an adhesion portion and a release portion are provided on the elastic base member portion obtained by the above-described method, and thus, the restoring force preserving portion-bonded medical tape in the state where the residual shrink force generated in association with the forming shrinkage of the solution polymer is reduced or eliminated is completed. Note that, the "restoring force associated with a shape change in a direction opposite to the residual shrink force generated in association with the forming shrinkage" is hereinafter referred to as a "shape change restoring force.

The restoring force preserving portion-bonded medical tape manufactured as described above is used in the following sequence: 1) remove the release portion; 2) apply the tape on a skin with the adhesion portion; and 3) remove the restoring force preserving portion. In this manner, by dealing with the forming shrinkage from a manufacturing stage, the restoring force preserving portion-bonded medical tape in the state where the residual shrink force generated in association with the forming shrinkage of the solution polymer is reduced or eliminated can be used. Thus, the reduction of the residual shrink force of the restoring force preserving portion-bonded medical tape when it is manufactured becomes an effective means to reduce the force that continuously shrinks the skin caused by the residual shrink force of the conventional support-bonded medical tape using inelastic material as the support, in particular, the medical tape that has the forming shrinkage by using the solution polymer as a raw material and simultaneously performing the film formation and the lamination in the manufacturing process and reduce persistent skin irritation during the application duration.

Introducing these effective means to the restoring force preserving portion-bonded medical tape as a function ensures applying the medical tape on a skin with the residual shrink force of the medical tape being reduced when in use of the medical tape, reducing the force that continuously shrinks the skin due to the residual shrink force of the medical tape, and thus, alleviating the persistent skin irritation during the application duration caused by the residual shrink force, thereby ensuring an application on a skin that exhibits an excessive reaction even with an insignificant irritation. Furthermore, it can be expected that a skin trouble, a medical instrument pressure-related wound, or the like caused by the persistent skin irritation during the application duration is prevented. From this viewpoint, it would be recognized that the conventional support-bonded medical tape using inelastic material as the support, in particular, the medical tape that has the forming shrinkage by using the solution polymer as the raw material and simultaneously performing the film formation and the lamination in the manufacturing process fail to consider the residual shrink force associated with the forming shrinkage.

Therefore, the present inventor selected the material that can be laminated with the restoring force preserving portion from the materials that is harden to form the film after being applied to the upper layer of the restoring force preserving portion as the material of the solution polymer that will later become the elastic base member portion in order to provide a conventional support-bonded medical tape using inelastic material as the support, in particular the restoring force preserving portion-bonded medical tape having a function to reduce the residual shrink force associated with the forming shrinkage of the medical tape with the forming shrinkage by using a solution polymer as a raw material and simultaneously performing a film formation and a lamination in a manufacturing process. Furthermore, the present inventor selected a material that can be used for medical purposes and has excellent waterproofness, moisture permeability, skin followability, etc. from the materials functioning as the elastic base member portion after the film formation. Next, the present inventor selected the material having inelastic, flexible, and restorable functions, as the material of the restoring force preserving portion, from materials that the solution polymer serving as the elastic base member portion can be applied to the upper layer thereof and the solution polymer can be formed into the film and laminated at the same time. In addition, the present inventor selected a medical adhesive material having a function to apply and hold the elastic base member portion to the skin, and having less adhesive residue and keratin damage during peeling, as the material of the adhesion portion, and selected the material of having a function to protect the adhesion portion, as the material of the release portion. The inventor came up with an idea of configuring the restoring force preserving portion-bonded medical tape using the functions of each material.

By combining these materials, in the manufacturing process of the restoring force preserving portion-bonded medical tape, a solution polymer serving as the elastic base member portion having an elastic function is applied to an upper layer of the restoring force preserving portion bent into an approximately arc shape having a projected cross-sectional shape by an external force using a work table having a recessed cross-sectional shape, and a film formation of the elastic base member portion and a lamination of the restoring force preserving portion and the elastic base member portion are simultaneously performed to complete the film formation, obtain the elastic base member portion, and obtain an approximately arc-shaped two-layer structure having a projected cross-sectional shape, which is composed of the restoring force preserving portion and the elastic base member portion. After that, the external force applied to the restoring force preserving portion is removed by moving the two-layer structure from the recess-shaped work table to a work table having a horizontal cross-sectional shape to exert a restorability that the restoring force preserving portion has and obtain a two-layer structure composed of the elastic base member portion in a state where a residual shrink force generated in association with a forming shrinkage of the solution polymer is reduced by a restoring force associated with a shape change in a direction opposite to the residual shrink force generated in association with the forming shrinkage of the solution polymer and the restoring force preserving portion. This ensures obtaining the elastic base member portion in a state where the residual shrink force generated in association with the forming shrinkage of the solution polymer is reduced or eliminated. Then, an adhesion portion and a release portion are provided on the elastic base member portion obtained by the above-described method, and thus, it is possible to manufacture the restoring force preserving portion-bonded medical tape in the state where the residual shrink force generated in association with the forming shrinkage of the solution polymer is reduced or eliminated. Accordingly, the present invention have been completed in view of the knowledge that a medical tape can be provided in which: when the restoring force preserving portion-bonded medical tape is used, it is applied to the skin with the adhesion portion; the residual shrink force and the shape change restoring force preserved in the elastic base member portion of the restoring force preserving portion-bonded medical tape can be simultaneously released by removing the restoring force preserving portion; the restoring force preserving portion-bonded medical tape can have, as a function, means to reduce the force that causes the skin to shrink continuously due to the residual shrink force of the medical tape accompanying the forming shrinkage by simultaneously releasing the residual shrink force and the conflicting shape change restoring force; and the persistent skin irritation during the application duration caused by the residual shrink force is alleviated, thereby ensuring an application on a skin that exhibits an excessive reaction even with an insignificant irritation.

A medical tape obtained by the method for manufacturing of the present invention includes, in the following order, the restoring force preserving portion, the elastic base member portion, the adhesion portion, and the release portion. In a manufacturing process, the solution polymer serving as the elastic base member portion having an elastic function is applied to an upper layer of the restoring force preserving portion bent into an approximately arc shape having a projected cross-sectional shape by an external force using a work table having a recessed cross-sectional shape, and a film formation of the elastic base member portion and a lamination of the restoring force preserving portion and the elastic base member portion are simultaneously performed to complete the film formation, obtain the elastic base member portion, and obtain an approximately arc-shaped two-layer structure having a projected cross-sectional shape, which is composed of the restoring force preserving portion and the elastic base member portion. Subsequently, the external force applied to the restoring force preserving portion is removed by moving the two-layer structure from the recess-shaped work table to a work table having a horizontal cross-sectional shape to exert a restorability that the restoring force preserving portion has and obtain a two-layer structure composed of the elastic base member portion in a state where a residual shrink force generated in association with a forming shrinkage of the solution polymer is reduced by a restoring force associated with a shape change in a direction opposite to the residual shrink force generated in association with the forming shrinkage of the solution polymer and the restoring force preserving portion. This step ensures obtaining the elastic base member portion in a state where the residual shrink force generated in association with the forming shrinkage of the solution polymer is reduced or eliminated. Then, an adhesion portion and a release portion are provided on the elastic base member portion obtained by the above-described method, and thus, the restoring force preserving portion-bonded medical tape in the state where the residual shrink force generated in association with the forming shrinkage of the solution polymer is reduced or eliminated can be used.

Note that, in the manufacturing method of the medical tape of the present invention, the solution polymer serving as the elastic base member portion is applied to the upper layer of the restoring force preserving portion bent into an approximately arc shape having a projected cross-sectional shape by an external force, and a film formation of the elastic base member portion and a lamination of the restoring force preserving portion and the elastic base member portion are simultaneously performed to obtain an approximately arc-shaped or approximately bow-shaped two-layer structure having a projected cross-sectional shape, which is composed of the restoring force preserving portion and the elastic base member portion. At this time, for a degree of bending the restoring force preserving portion, the restoring force preserving portion is preferably bent in such a degree that the residual shrink force associated with the forming shrinkage in the elastic base member portion can be eliminated by a force required for eliminating the residual shrink force associated with the forming shrinkage of the elastic base member portion, that is, the shape change restoring force generated in the restoring force preserving portion. However, since a degree of residual shrink force associated with the forming shrinkage as a cause is insignificant so as to be described as of a level of magnifying lens or microscope, not as of a level of naked eye, the degree of bending the restoring force preserving portion may be insignificant, and as long as the elastic base member portion has an approximately arc shape or approximately bow shape having a projected cross-sectional shape even slightly, the effect of the present invention can be sufficiently obtained even if it is insignificant. Also, it is only necessary for the material of the restoring force preserving portion to have inelastic, flexible, and restorable functions, and the material, the shape and the like may be optional. The material is not specifically limited as long as the effect of the present invention can be provided.

Hereinafter, although the examples of the present invention will be explained in detail using the drawings, the present invention is not limited thereto. In an appropriate selection/combination of the material constructing the restoring force preserving portion-bonded medical tape, and a manufacturing process of the present invention, a restoring force preserving portion (FIG. 3) is bent into an approximately arc shape having a projected cross-sectional shape by an external force (FIG. 4), a solution polymer serving as an elastic base member portion having an elastic function is applied to the upper layer of the restoring force preserving portion, and a film formation of the elastic base member portion and a lamination of the restoring force preserving portion and the elastic base member portion are simultaneously performed to complete the film formation, obtain the elastic base member portion, and obtain an approximately arc-shaped two-layer structure (FIG. 5) having a projected cross-sectional shape, which is composed of the restoring force preserving portion and the elastic base member portion. At this time, a residual shrink force (internal stress) associated with a forming shrinkage is generated in the elastic base member portion. Subsequently, the external force applied to the restoring force preserving portion is removed to exert a restorability that the restoring force preserving portion has and obtain a two-layer structure (FIG. 6) composed of the elastic base member portion in a state where the residual shrink force generated in association with the forming shrinkage of the solution polymer is reduced by a restoring force associated with a shape change in a direction opposite to the residual shrink force generated in association with the forming shrinkage of the solution polymer and the restoring force preserving portion. Subsequently, an adhesion portion having a function to apply and hold the elastic base member portion on a skin is laminated on the elastic base member portion, a release portion having a function to protect the adhesion portion is laminated on the adhesion portion (FIG. 7), and thus, the restoring force preserving portion-bonded medical tape is completed. After that, the release portion is removed to apply the tape on a skin with the adhesion portion, and the residual shrink force as well as a shape change restoring force preserved in the elastic base member portion of the restoring force preserving portion-bonded medical tape are released by removing the restoring force preserving portion. Basically, by simultaneously releasing the residual shrink force and the conflicting shape change restoring force, the force that causes the skin to shrink continuously due to the residual shrink force of the medical tape accompanying the forming shrinkage is reduced, and the persistent skin irritation during the application duration caused by the residual shrink force is alleviated. In the present invention, it is essential to reduce the residual shrink force during manufacturing of the restoring force preserving portion-bonded medical tape.

The restoring force preserving portion-bonded medical tape according to the first embodiment of the present invention illustrated in FIG. 3 to FIG. 7 is configured of a restoring force preserving portion 1 having inelastic, flexible, and restorable functions, an elastic base member portion 2 having an elastic function, an adhesion portion 3 having a function to apply and hold the elastic base member portion 2 on a skin, and a release portion 4 having a function to protect the adhesion portion 3.

Figure 3:
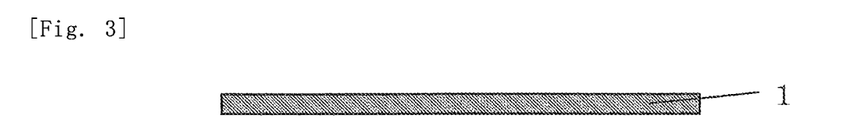
FIG. 3 is a schematic cross-sectional view of a restoring force preserving portion 1 used for a medical tape according to a first embodiment of the present invention.
Figure 4:
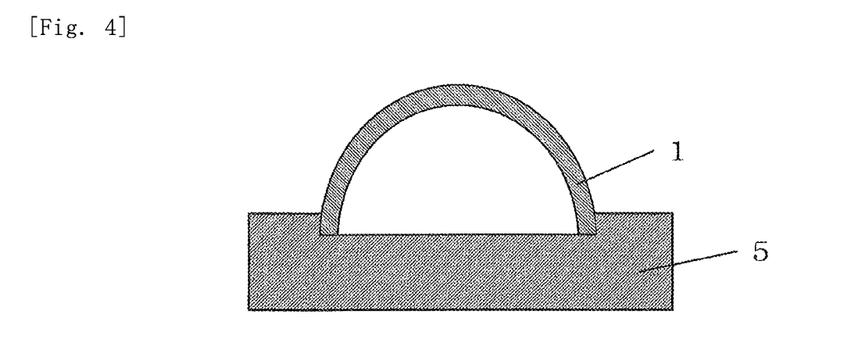
FIG. 4 is a drawing illustrating a manufacturing process of the medical tape according to the first embodiment of the present invention and is a schematic cross-sectional view illustrating a state where the restoring force preserving portion 1 is bent into an approximately arc shape having a projected cross-sectional shape by an external force using a recess-shaped work table 5.
Figure 5:
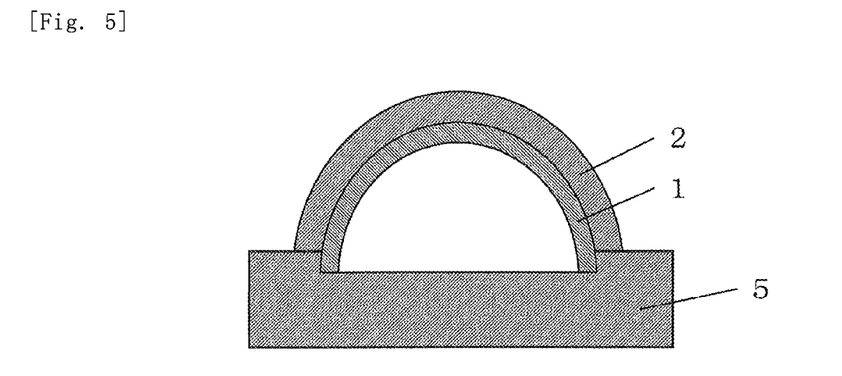

FIG. 3 is a schematic cross-sectional view of the restoring force preserving portion 1 used for the medical tape according to the first embodiment of the present invention. FIG. 4 and FIG. 5 are schematic cross-sectional views illustrating manufacturing processes of the medical tape according to the first embodiment of the present invention. In the restoring force preserving portion-bonded medical tape according to the first embodiment, in the manufacturing process, the plate-shaped restoring force preserving portion 1 (FIG. 3) having inelastic, flexible, and restorable functions is placed on the recess-shaped work table 5 so as to draw an approximately arc-shaped curve having a projected cross-sectional shape in a longitudinal direction by an external force (FIG. 4), a solution polymer that will later become the elastic base member portion 2 is applied to the upper layer of the restoring force preserving portion 1, and a film formation of the elastic base member portion 2 and a lamination of the restoring force preserving portion 1 and the elastic base member portion 2 are simultaneously performed to complete the film formation, obtain the elastic base member portion 2, and obtain an approximately arc-shaped two-layer structure having a projected cross-sectional shape, which is composed of the restoring force preserving portion 1 and the elastic base member portion 2, as FIG. 5 illustrates the state of this step. Note that the reference numeral 1 denotes the restoring force preserving portion, the reference numeral 2 denotes the elastic base member portion, and the reference numeral 5 denotes the recess-shaped work table.

Figure 6:
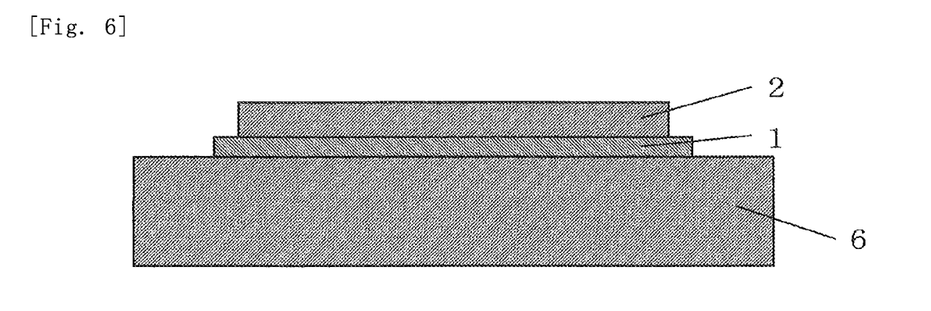

FIG. 6 is a schematic cross-sectional view illustrating a manufacturing process of the medical tape according to the first embodiment of the present invention. The external force applied to the restoring force preserving portion 1 is removed by moving the two-layer structure obtained in the previous step from the recess-shaped work table to a work table having a horizontal cross-sectional shape to exert a restorability that the restoring force preserving portion 1 has and obtain a two-layer structure composed of the elastic base member portion 2 in a state where a residual shrink force generated in association with a forming shrinkage of the solution polymer is reduced by a restoring force associated with a shape change in a direction opposite to the residual shrink force generated in association with the forming shrinkage of the solution polymer and the restoring force preserving portion 1. Note that the reference numeral 1 denotes the restoring force preserving portion, the reference numeral 2 denotes the elastic base member portion, and the reference numeral 6 denotes the work table having a horizontal cross-sectional shape.

Figure 7:
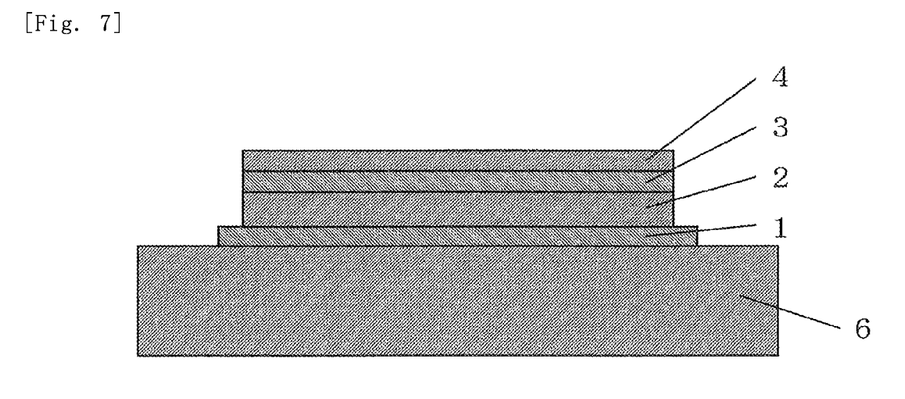
FIG. 7 is a schematic cross-sectional view illustrating a manufacturing process of the medical tape according to the first embodiment of the present invention and illustrates a state where an adhesive is applied to an upper layer of the elastic base member portion 2 to configure an adhesion portion 3, and a release portion 4 is provided on an upper layer of the adhesion portion 3.

FIG. 7 is a schematic cross-sectional view illustrating a manufacturing process of the medical tape according to the first embodiment of the present invention. The adhesion portion 3 having a function to apply and hold the elastic base member portion 2 on a skin is laminated on the upper layer of the elastic base member portion 2 illustrated in FIG. 6, and the release portion 4 having a function to protect the adhesion portion 3 is laminated on the upper layer of the adhesion portion 3, and thus, the restoring force preserving portion-bonded medical tape is completed. Note that the reference numeral 1 denotes the restoring force preserving portion, the reference numeral 2 denotes the elastic base member portion, the reference numeral 3 denotes the adhesion portion, the reference numeral 4 denotes the release portion, and the reference numeral 6 denotes the work table having a horizontal cross-sectional shape.

In the restoring force preserving portion-bonded medical tape, in a manufacturing process, a shape change restoring force is generated in the restoring force preserving portion 1 (FIG. 4), and the shape change restoring force is preserved in the elastic base member portion 2 (FIG. 6). The restoring force preserving portion-bonded medical tape is used in the following sequence: 1) remove the release portion; 2) apply the tape on a skin with the adhesion portion; and 3) remove the restoring force preserving portion. In the restoring force preserving portion-bonded medical tape, by removing the restoring force preserving portion when in use, the residual shrink force and the shape change restoring force preserved in the elastic base member portion are simultaneously released. The residual shrink force is a force that causes the elastic base member portion of the restoring force preserving portion-bonded medical tape to shrink, and the shape change restoring force is a force that acts in a direction opposite to the residual shrink force. By simultaneously releasing the residual shrink force and the conflicting shape change restoring force, the medical tape is applied on a skin in a state where the residual shrink force of the medical tape is reduced when in use, and the force that continuously shrinks the skin due to the residual shrink force of the medical tape can be reduced. Accordingly, in the restoring force preserving portion-bonded medical tape of the present invention, by introducing the means for reducing the force that continuously shrinks the skin caused by the residual shrink force associated with the forming shrinkage to a medical tape as a function, it is possible to apply the medical tape on the skin in the state where the residual shrink force of the medical tape is reduced when in use, and therefore, it is possible to reduce the force that continuously shrinks the skin due to the residual shrink force of the medical tape, and alleviate the persistent skin irritation during the application duration caused by the residual shrink force. This ensures an application on the skin that exhibits an excessive reaction even when a degree of residual shrink force as a cause is an insignificant irritation so as to be described as of a level of magnifying lens or microscope, not as of a level of naked eye, thereby ensuring providing a medical tape, an adhesive skin patch, and the like of low irritation.

Specifically, in the first embodiment of the present invention, in the manufacturing process, the restoring force preserving portion 1 is composed of an inelastic plastic film having flexible and restorable functions dealing with a shape change of the restoring force preserving portion 1 in the manufacturing process of the restoring force preserving portion-bonded medical tape and is placed so as to draw an approximately arc-shaped curve having a projected cross-sectional shape in a longitudinal direction by an external force using a work table having a recessed cross-sectional shape. A mixed liquid (a urethane resin liquid and a cross-linking agent liquid) serving as a raw material of a polyurethane film that will later become the elastic base member portion 2 is applied to one surface (upper layer) of the restoring force preserving portion 1 and a film formation of the elastic base member portion 2 and a lamination of the restoring force preserving portion 1 and the elastic base member portion 2 are simultaneously performed to complete the film formation, obtain the elastic base member portion 2, and obtain an approximately arc-shaped two-layer structure (FIG. 5) having a projected cross-sectional shape, which is composed of the restoring force preserving portion 1 and the elastic base member portion 2. Subsequently, the external force applied to the restoring force preserving portion 1 is removed by moving the two-layer structure from the recess-shaped work table 5 to the work table 6 having a horizontal cross-sectional shape to exert a restorability that the restoring force preserving portion 1 has and obtain a two-layer structure (FIG. 6) composed of the elastic base member portion 2 in a state where a residual shrink force generated in association with a forming shrinkage of the solution polymer is reduced by a restoring force associated with a shape change in a direction opposite to the residual shrink force generated in association with the forming shrinkage of the solution polymer and the restoring force preserving portion 1. Subsequently, through the step in which the adhesion portion 3 having a function to apply and hold the elastic base member portion 2 on a skin is laminated on the upper layer of the elastic base member portion 2 and the release portion 4 having a function to protect the adhesion portion 3 is laminated on the adhesion portion 3, the restoring force preserving portion-bonded medical tape of the present invention in which the residual shrink force as well as the shape change restoring force are preserved in the elastic base member portion 2 is completed.

While in the first embodiment, the mixed liquid (the urethane resin liquid and the crosslinking agent liquid) serving as the raw material of the polyurethane film is used as the material of the elastic base member portion, any material that can be laminated with the restoring force preserving portion after being applied to one surface of the restoring force preserving portion and at the same time of being hardened to form a film and that can cause the shrink force associated with the forming shrinkage to remain in the elastic base member portion may be used as the material of the elastic base member portion. The material and the shape are not restricted as long as they are suitable for medical treatment. While the acrylic adhesive is used for the material of the adhesion portion, the material of the adhesion portion may be any adhesive that has a function to apply and hold the elastic base member portion on the skin and is usable for medical treatment, and the adhesive may be applied partly or entirely to correspond to the usage, and thus, the material and the shape are not restricted. As the material of the restoring force preserving portion, an inelastic plastic film having a flexible function dealing with a shape change of the restoring force preserving portion-bonded medical tape and a restorable function including a restoring force slightly superior to the residual shrink force (internal stress) generated by the forming shrinkage associated with hardening of the mixed liquid serving as the raw material of the polyurethane film is used in a state of a single plate that is not physically separated, and all the residual shrink force associated with the forming shrinkage is eliminated. However, the degree of residual shrink force associated with the forming shrinkage that this patent is solving is not of a level of naked eye, but is of a level of magnifying lens or microscope. Therefore, the restoring force included in the restoring force preserving portion may be such a degree that the residual shrink force associated with the forming shrinkage can be brought into a state of being slightly reduced. The functions of the restoring force preserving portion may be included by a combination of materials. For example, by dividing a plastic film into two plates and covering its boundary in part or in whole with a single-plated material that is an identical material and is not physically separated, a structure laminated in a peelable state when in use of the restoring force preserving portion-bonded medical tape may be used as the restoring force preserving portion. As long as the functions as the restoring force preserving portion are included, the material and the shape of the restoring force preserving portion may be optional, and other functions may be included in the restoring force preserving portion and the upper layer of the restoring force preserving portion. The material and the shape are not restricted to correspond to the usage. Further, it is only necessary for the release portion to have a function to protect the adhesion portion, and the function may be included in a package. Note that, the selection and combination of the material constructing each part of the restoring force preserving portion-bonded medical tape may be optional to correspond to the usage, design, convenience, and the like, and is not particularly limited as long as the effects of the present invention can be obtained.

Furthermore, as the restoring force preserving portion, a material having an appropriate restorability may be selected from inelastic materials having flexible and restorable functions, formed into an approximately arc shape or approximately bow shape having a recessed cross-sectional shape in a width direction, and placed so as to draw a curve having a projected cross-sectional shape in an approximately arc shape or approximately bow shape in a longitudinal direction while maintaining a horizontal cross-sectional shape in the longitudinal direction by an appropriate external force, the solution polymer serving as the elastic base member portion may be applied to its upper layer, and a film formation of the elastic base member portion and a lamination of the restoring force preserving portion and the elastic base member portion may be simultaneously performed to complete the film formation, obtain the elastic base member portion, and obtain an approximately arc-shaped or approximately bow-shaped two-layer structure having a projected cross-sectional shape, which is composed of the restoring force preserving portion and the elastic base member portion. By removing the external force applied to the restoring force preserving portion from the two-layer structure obtained by the above-described method in the next step, the shape change restoring force to both directions of the width direction and the longitudinal direction can be included in the elastic base member portion, and the elastic base member portion in a state where the residual shrink force generated in association with the forming shrinkage of the solution polymer is reduced from the two directions can be obtained. Note that "placed so as to draw a curve" is a wording expressing of being placed in a manner that the shape is not horizontal but an approximately arc shape or approximately bow shape. As described above, while the means for including the shape change restoring force to both directions of the width direction and the longitudinal direction in the elastic base member portion is described as one example, the direction to which the shape change restoring force is included may be optional to correspond to the usage, convenience, and the like. The material, the shape and the like of the restoring force preserving portion may be optional to correspond to the usage, design, convenience, and the like, and is not particularly limited as long as the effects of the present invention can be obtained.

The medical tape obtained by the manufacturing method of the present invention illustrated in FIG. 3 to FIG. 7 all has a basic structure of the present invention. Such a configuration ensures simultaneously releasing the residual shrink force and the shape change restoring force preserved in the elastic base member portion of the restoring force preserving portion-bonded medical tape, which is a force that acts in a direction opposite to the residual shrink force by removing the restoring force preserving portion when in use of the restoring force preserving portion-bonded medical tape, and manufacturing the medical tape in which the residual shrink force associated with the forming shrinkage of the solution polymer is reduced in the manufacturing process by introducing the means for reducing the force to continuously shrink the skin caused by the residual shrink force associated with the forming shrinkage of the conventional support-bonded medical tape using inelastic material as the support. Therefore, the restoring force preserving portion-bonded medical tape manufactured using the film-forming base portion can alleviate the persistent skin irritation during the application duration caused by the residual shrink force by applying the medical tape on a skin in the state where the residual shrink force associated with the forming shrinkage is reduced and reducing the force to continuously shrink a skin caused by the residual shrink force associated with the forming shrinkage of the restoring force preserving portion-bonded medical tape. This ensures an application on the skin that exhibits an excessive reaction even when a degree of residual shrink force associated with the forming shrinkage as a cause is an insignificant irritation so as to be described as of a level of magnifying lens or microscope, not as of a level of naked eye, thereby ensuring providing a medical tape, an adhesive skin patch, and the like of low irritation. Preventions of inflammation in sebaceous glands or sweat glands, inflammation in hair roots and surrounding tissues, medical instrument pressure-related wounds caused by poor blood circulation of cells of skin, capillary blood vessels, and the like caused by pressure, and the like can be expected.

While the example where the medical tape has a shape of rectangular has been described in the first embodiment above, any shape can be selected for the shape of the medical tape to correspond to the usage. For example, a rolled shape and a sheet shape are possible, and a shape that fits each part of body is also possible. While the medical tape is basically configured of the restoring force preserving portion, the elastic base member portion, the adhesion portion, and the release portion, a gauze, a pad, and the like may be provided on the lower layer of the adhesion portion to correspond to the usage, design, convenience, and the like. Note that while the present invention is based on the application on a skin in a closely contacted manner, the medical tape may be applied via a protecting material and the like for protecting the skin from the medical adhesive and the like in some cases.

While all the residual shrink force associated with the forming shrinkage is preferred to be eliminated, a state where it is slightly reduced is also possible. This is because the degree of residual shrink force associated with the forming shrinkage that this patent is solving is not of a level of naked eye, but is of a level of magnifying lens or microscope. In this description, the process from the manufacturing of the medical tape to the application is described, and "when in use" and "during application duration" are defined as follows. "When in use" represents the duration from removing the release portion, applying on a skin, until removing the support portion following the procedure of using the medical tape. "During application duration" represents the duration where the restoring force preserving portion-bonded medical tape is continuously applied.

Note that the function of the medical tape according to the present invention is effectively applied to a medical tape aiming to be applied to a human body. For example, since a skin irritation hypersensitivity patient severely reacts to even an insignificant skin irritation, the use of medical tapes containing percutaneously absorbable drugs is postponed in some cases. However, since it is possible to alleviate the insignificant skin irritation by using the medical tape according to the present invention, the medical tape according to the present invention can be used as a patch by blending percutaneously absorbable drugs in the adhesive portion. Providing a pad to the medical tape of the present invention ensures a usage as a treatment product.

INDUSTRIAL APPLICABILITY

The restoring force preserving portion-bonded medical tape obtained by the method of production of the present invention has an extremely high effect of alleviating the persistent skin irritation during the application duration caused by the residual shrink force associated with the forming shrinkage of the support-bonded medical tape using inelastic material as the support obtained by the prior art, in particular, the medical tape that has the forming shrinkage by using the solution polymer as the raw material and simultaneously performing the film formation and the lamination in the manufacturing process so as to be applicable on the skin that exhibits an excessive reaction even with an insignificant irritation. In addition, preventions of a skin trouble, a medical instrument pressure-related wound, and the like caused by the persistent skin irritation during the application duration can be expected. Furthermore, it is possible to provide a low-irritation medical tape, patch or the like. Therefore, the medical tape according to the present invention will greatly contribute to the medical industries.

REFERENCE SIGNS LIST 1 restoring force preserving portion
2 elastic base member portion
3 adhesion portion
4 release portion
5 recess-shaped work table
6 work table having a horizontal cross-sectional shape

The invention claimed is:

1. A method for manufacturing a medical tape, comprising:
applying a solution polymer serving as an elastic base member portion having an elastic function to an upper layer of a restoring force preserving portion bent into a shape or shape having a projected cross-sectional shape by an external force and simultaneously performing a film formation of the elastic base member portion and a lamination of the restoring force preserving portion and the elastic base member portion to complete the film formation, obtaining the elastic base member portion, and obtaining a shaped or shaped two-layer structure having a projected cross-sectional shape, the two-layer structure being composed of the restoring force preserving portion and the elastic base member portion; and subsequently, removing the external force applied to the restoring force preserving portion to exert a restorability that the restoring force preserving portion has and obtaining a two-layer structure composed of the elastic base member portion and the restoring force preserving portion, the elastic base member portion being in a state where a residual shrink force generated in association with a forming shrinkage of the solution polymer is reduced by a restoring force associated with a shape change in a direction opposite to the residual shrink force generated in association with the forming shrinkage of the solution polymer.

* * * * *